(12) United States Patent
Sperl et al.

(10) Patent No.: US 6,211,177 B1
(45) Date of Patent: Apr. 3, 2001

(54) METHOD FOR TREATING NEOPLASIA BY EXPOSURE TO SUBSTITUTED 2-ARYL-BENZIMIDAZOLE DERIVATIVES

(75) Inventors: Gerhard Sperl, North Wales, PA (US); Ulrich Ixkes, Stockton, CA (US); Rifat Pamukcu, Spring House; Gary A. Piazza, Doylestown, both of PA (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 09/200,378

(22) Filed: Nov. 24, 1998

(51) Int. Cl.$^7$ ............. A61K 31/53; A61K 31/495; A61K 31/505; A61K 31/44; A61K 31/415

(52) U.S. Cl. ............. 514/241; 514/242; 514/255.05; 514/269; 514/333; 514/338; 514/394

(58) Field of Search ............. 514/394, 333, 514/338, 269, 255.05, 241, 242

(56) References Cited

U.S. PATENT DOCUMENTS

| | | |
|---|---|---|
| 4,950,680 | 8/1990 | Taylor et al. . |
| 5,552,426 * | 9/1996 | Lunn et al. ............. 514/394 |
| 5,696,159 | 12/1997 | Gross et al. . |
| 5,767,138 * | 6/1998 | Camden ............. 514/365 |
| 6,025,379 * | 2/2000 | Iyengar et al. ............. 514/394 |

FOREIGN PATENT DOCUMENTS

| | | |
|---|---|---|
| WO 95/19978 | 7/1995 | (WO) . |
| WO 00/15222 | 3/2000 | (WO) . |

OTHER PUBLICATIONS

Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104, (1998).

Chang, W. et al., Sulindac Sulfone Modulates the Expression and Cellular Localization of b–Catenin in Human Colon Carcinoma Cells, Digestive Disease Week, Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Korinek, V. et al., Constitutive Transcriptional Activation by a β–Catenin–Tcf Complex in APC$^{+/+}$ Colon Carcinoma, Science, vol. 275, pp. 1784–1786, Mar. 21, 1997.

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Morin, P. et al., Activation of β–Catenin–Tcf Signaling in Colon Cancer by Mutations in β–Catenin or APC, Science, vol. 275, pp. 1787–1789, Mar. 21, 1997.

Peifer, M., β–Catenin as Oncogene: The Smoking Gun, Science, vol. 275, pp. 1752–1753, Mar. 21, 1997.

Rubinfeld, B. et al., Stabilization of β–Catenin by Genetic Defects in Melanoma Cell Lines, Science, vol. 275, pp. 1790–1792, Mar. 21, 1997.

* cited by examiner

*Primary Examiner*—Jerome D. Goldberg
(74) *Attorney, Agent, or Firm*—Robert W. Stevenson

(57) ABSTRACT

A method for inhibiting neoplasia, particularly cancerous and precancerous lesions, by exposing the affected cells to substituted 2-aryl-benzimidazoles.

6 Claims, No Drawings

METHOD FOR TREATING NEOPLASIA BY EXPOSURE TO SUBSTITUTED 2-ARYL-BENZIMIDAZOLE DERIVATIVES

TECHNICAL FIELD

This invention relates to methods for inducing or promoting apoptosis and for arresting uncontrolled neoplastic cell proliferation, methods that are specifically useful in the arresting and treatment of neoplasias, including precancerous and cancerous lesions.

BACKGROUND OF THE INVENTION

Pharmaceuticals that are effective against early stage neoplasias comprise an emerging and expanding area of research and potential commercial development. Such pharmaceuticals can delay or arrest development of precancerous lesions into cancers. Each year in the United States alone, untold numbers of people develop precancerous lesions, which exhibit a strong statistically significant tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), cervical displasia (cervical cancer) and other such neoplasms.

Such compounds and methods are particularly beneficial to sub-populations of patients who repeatedly develop precancerous lesions, and therefore have a statistically higher probability of getting cancer. Many cancer types (e.g., breast, colon, prostate etc.) have such patient sub-populations.

The search for drugs useful for treating and preventing neoplasias in their earliest stages is intensive because chemotherapy and surgery on cancer itself is often not effective, and current cancer chemotherapy has severe side effects. Such cancer-preventative compounds are also envisaged for recovered cancer patients who retain a risk of cancer reoccurrence, and even for cancer patients who would benefit from compounds that selectively induce apoptosis in neoplastic, but substantially not in normal cells.

Because it is believed that chronic administration of cancer-preventative pharmaceuticals is necessary to inhibit or arrest the development of neoplasia, standard cancer chemotherapeutic drugs are not considered appropriate drugs for cancer chemoprevention because whatever cancer preventative (as opposed to cancer-fighting) capabilities those drugs may possess do not outweigh their severe side effects. Most standard chemotherapeutics are now believed to kill cancer cells by inducing apoptosis (also sometimes referred to as "programmed cell death"). Apoptosis naturally occurs in many tissues in the body. Apoptosis plays a critical role in tissue homeostasis, that is, it ensures that the number of new cells produced are correspondingly offset by an equal number of cells that die. Apoptosis is especially pronounced in self-renewing tissues such as bone marrow, immune cells, gut, and skin. For example, the cells in the intestinal lining divide so rapidly that the body must eliminate cells after only three days to protect and prevent the overgrowth of the intestinal lining.

Standard chemotherapeutics promote apoptosis not only in cancer cells, but also in normal human tissues, and therefore have a particularly severe effect on tissues where apoptosis is especially pronounced (e.g. hair, gut and skin). The results of those effects include hair loss, weight loss, vomiting and bone marrow immune suppression. Thus, standard chemotherapeutics are inappropriate for cancer prevention, particularly if chronic administration is indicated.

Several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the continued prophylactic use of currently available NSAIDs, even in high colon cancer-risk patients, is still marked by severe side reactions that include gastrointestinal irritations, perforations, ulceration and kidney toxicity believed to be produced by inhibition of prostaglandin synthetase activity ("PGE-2"). Such inhibition is a requirement for the NSAIDs anti-inflammatory action since elevated levels of PGE-2 are associated with inflammation. PGE-2 plays a protective function in the gastrointestinal tract, which is the reason such gastric side effects arise with chronic NSAID therapy, which is rarely indicated for arthritis sufferers, acute therapy being the norm for them. However, chronic administration of sulindac is important for high cancer-risk patients to eliminate and prevent future polyps which causes gastric side effects in many such patients. Once NSAID treatment is terminated due to such complications, the neoplasms return, particularly in high risk patients.

Compounds such as those disclosed in U.S. Pat. No. 5,643,959 have exhibited advantages in the treatment of neoplastic lesions since such compounds have been shown to induce apoptosis in neoplastic cells but not in normal cells in humans. Thus, the severe side effects due to induction of apoptosis in normal cells by conventional chemotherapeutics are avoided by these novel therapeutics (see, Van Stolk, et al., *Gastroenterology*, 112 (4): A673, 1997). In addition, such compounds do not exhibit the gastric side effects associated with NSAIDs since such compounds do not substantially inhibit PGE-2. More potent compounds with such neoplasia specificity but without substantial PGE-2 activity are desirable.

SUMMARY OF THE INVENTION

This invention represents potent compounds that induce apoptosis in neoplastic cells (but not substantially in normal cells), for treating patients with neoplastic lesions without substantially inhibiting PGE-2. This invention also involves methods for inducing such specific apoptosis in neoplastic cells by exposing such cells to a pharmacologically effective amount of those compounds described below to a patient in need of such treatment. Such compositions are effective in modulating apoptosis and modulating the growth of neoplasms, but are not suffering from the side effects of conventional chemotherapeutics and NSAIDs.

DETAILED DESCRIPTION OF THE INVENTION

As discussed above, the present invention utilizes compounds of Formula I below

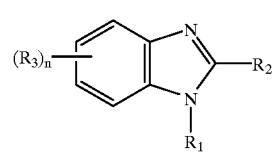

I wherein
  $R_1$ is selected from a group consisting of hydrogen, lower alkyl, —$(CH_2)_x$—C(O)—$OR_4$, —$(CH_2)_x$—C(O)—

NH—(CH$_2$)$_y$—R$_5$, (CH$_2$)$_x$—S(O)$_m$—R$_6$ or substituted or unsubstituted benzyl, wherein said substituents are one or two independently selected from a group consisting of halogen, lower alkyl, lower alkoxy or phenyl;

R$_2$ is substituted or unsubstituted aryl, wherein said aryl group is selected from the group consisting of phenyl, benzyl, pyridyl, pyrimidyl, pyrazinyl, imidazolyl, indolyl, triazinyl, tetrazolyl, thiophenyl, furanyl, thiazolyl, pyrazolyl, or pyrrolyl, and wherein said substituents are one to three independently selected from the group consisting of halogen, lower alkyl or lower alkoxy;

R$_3$ is selected from a group consisting of halogen, lower alkoxy, lower alkyl, lower alkoxy carbonyl, carboxyl, substituted and unsubstituted carbamoyl, wherein said substituents are one or two independently selected from a group consisting of phenyl, benzyl, pyridyl, pyridylmethyl, or benzenesulfonyl;

R$_4$ is hydrogen or lower alkyl;

R$_5$ is selected from a group consisting of hydrogen, lower alkyl, benzyl, pyridyl, pyrimidinyl, pyrazinyl, imidazolyl, indolyl, triazinyl, tetrazolyl, thiophenyl, furanyl, thiazolyl, pyrazolyl, or pyrrolyl;

R$_6$ is substituted or unsubstituted phenyl, wherein said substituents are one to three independently selected from the group consisting of halogen, lower alkyl or lower alkoxy;

x is 0, 1, or 2;

m is 0, 1, or 2;

n is 0, 1 or 2; and y is 0, 1, or 2.

Preferred compounds of Formula I include those wherein:

R$_1$ is selected from a group consisting of hydrogen, lower alkyl, —(CH$_2$)$_x$—C(O)—OR$_4$, —(CH$_2$)$_x$—C(O)—NH—(CH$_2$)$_y$—R$_5$, or substituted or unsubstituted benzyl, wherein said substituents are one or two independently selected from the group consisting of halogen, lower alkoxy or phenyl;

R$_2$ is substituted or unsubstituted aryl, wherein said aryl group is selected from the group consisting of phenyl, benzyl, pyridyl, pyrimidyl, pyrazinyl, triazinyl, tetrazolyl, thiophenyl, furanyl, pyrazolyl, or pyrrolyl, and wherein said substituents are two or three independently selected from the group consisting of halogen and lower alkoxy;

R$_3$ is selected from a group consisting of halogen, lower alkoxy, lower alkoxy carbonyl, carboxyl, and substituted carbamoyl, wherein said substituent is one from a group consisting of phenyl, benzyl, pyridyl, pyridylmethyl, or benzenesulfonyl;

R$_4$ is lower alkyl;

R$_5$ is selected from a group consisting of benzyl, pyridyl, pyrimidinyl, pyrazinyl, triazinyl, tetrazolyl, thiophenyl, or furanyl;

R$_6$ is substituted phenyl, wherein said substituents are two or three independently selected from the group consisting of halogen or lower alkoxy;

x is 1 or 2;

m is 2;

n is 0 or 1; and y is 0 or 1.

Still more preferred compounds of this invention include those compounds of Formula I where R$_1$ is selected from a group consisting of hydrogen, —(CH$_2$)$_x$—C(O)—OR$_4$, —(CH$_2$)$_x$—C(O)—NH—(CH$_2$)$_y$—R$_5$, or substituted benzyl, wherein said substituent is one selected from the group consisting of halogen or lower alkoxy;

R$_2$ is substituted aryl, wherein said aryl group is selected from the group consisting of phenyl, benzyl, pyridyl, pyrimidyl, pyrazinyl, and triazinyl, and wherein said substituents are three independently selected from the group consisting of lower alkoxy;

R$_3$ is selected from a group consisting of halogen, lower alkoxy, and substituted carbamoyl, wherein said substituent is one from a group consisting of benzyl, pyridylmethyl, or benzenesulfonyl;

R$_4$ is lower alkyl;

R$_5$ is selected from a group consisting of benzyl and pyridyl;

R$_6$ is substituted phenyl, wherein said substituents are three independently selected from the group consisting of lower alkoxy;

x is 1;

m is 2;

n is 1; and y is 0.

The present invention is also a method of treating individuals with neoplastic lesions by administering a pharmacologically effective amount of an enterically coated pharmaceutical composition that includes compounds of this invention. Preferably, such compounds are administered without therapeutic amounts of an NSAID.

Also, the present invention is a method of inhibiting the growth of neoplastic cells by exposing the cells to an effective amount of compounds of Formula I, wherein R$_1$, R$_2$, R$_3$ and n are defined as above.

In still another form, the invention is a method of inducing apoptosis in human cells by exposing those cells to an effective amount of compounds of Formula I, wherein R$_1$, R$_2$, R$_3$ and n are defined as above where such cells are sensitive to these compounds.

Additionally, in yet another form, the invention is a method of treating a patient having a disease which would benefit from regulation of apoptosis by treating the patient with an effective amount of compounds of Formula I, wherein R$_1$ through R$_3$ etc. are defined as above. The regulation of apoptosis is believed to play an important role in diseases associated with abnormalities of cellular growth patterns such as benign prostate hyperplasia, neurodegenerative diseases such as Parkinson's disease, autoimmune diseases including multiple sclerosis and rheumatoid arthritis, infectious diseases such as AIDS, and other diseases, as well.

As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostate dysplasia, bronchial dysplasia, breast, bladder and/or skin and related conditions (e.g., actinic keratosis), whether the lesions are clinically identifiable or not.

As used herein, the term "cancerous" refers to lesions that are malignant. Examples include malignant melanomas, breast cancer, prostate cancer and colon cancer.

As used herein, the term "neoplasm" refers to both precancerous and cancerous lesions and hyperplasia.

As used herein, the term "halo" or "halogen" refers to chloro, bromo, fluoro and iodo groups, and the term "alkyl" refers to straight, branched or cyclic alkyl groups and to substituted aryl alkyl groups. The term "lower alkyl" refers to $C_1$ to $C_8$ alkyl groups.

The term "lower alkoxy" refers to alkoxy groups having from 1 to 8 carbons, including straight, branched or cyclic arrangements.

Compounds useful in this invention may be formulated into pharmaceutical compositions together with pharmaceutically acceptable carriers for oral administration in solid or liquid form, or for rectal or topical administration, although carriers for oral administration are most preferred. This invention also includes the use of salts and enantiomers of such compounds.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g., a box or bottle, or both) with suitable printed material (e.g., a package insert) containing indications, directions for use, etc.

The following general schemes can be used to obtain compounds of this invention.

Scheme 1

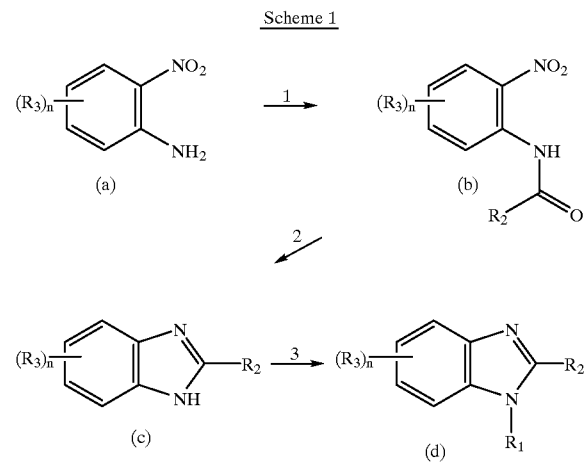

The solution of the substituted 2-nitroaniline (a) is charged with an acid chloride $R_2$—C(O)—Cl and is stirred over night at room temperature (reaction 1) to yield the amide (b). Iron (Fe) is added at once under reflux to the amide (b) in acetic acid (reaction 2). The obtained benzimidazole (c) in DMA is added in small portions to sodium hydride in DMA in an ice bath. This mixture is charged with the halogenide ($R_1$Hal) to yield the substituted 2-arylbenzimidazole (d) (reaction 3). In summary, the following reagents are used in scheme I:

1.) $R_2$—C(O)—Cl
2.) Iron (Fe), acetic acid
3.) NaH, DMA, $R_1$Hal

An alternative to obtain the benzimidazole (c) is demonstrated in scheme II:

Scheme II

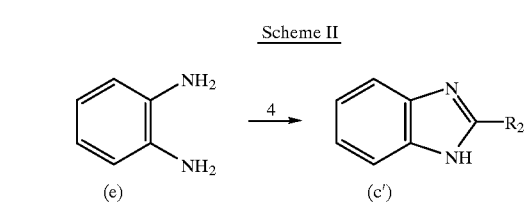

1,2-Phenylenedi amine (e) is charged with an aldehyde $R_2$—C(O)H in acetonitrile and 2,3-dichloro-5,6-dicyano-1,4-benzoquinone (DDQ) (reaction 4). Addition of sodium hydroxide gives the benzimidazole (c), which can be N-substituted to compound (d) as described in scheme I above.

For the synthesis of examples 10 to 21, the following scheme III is employed.

Scheme III

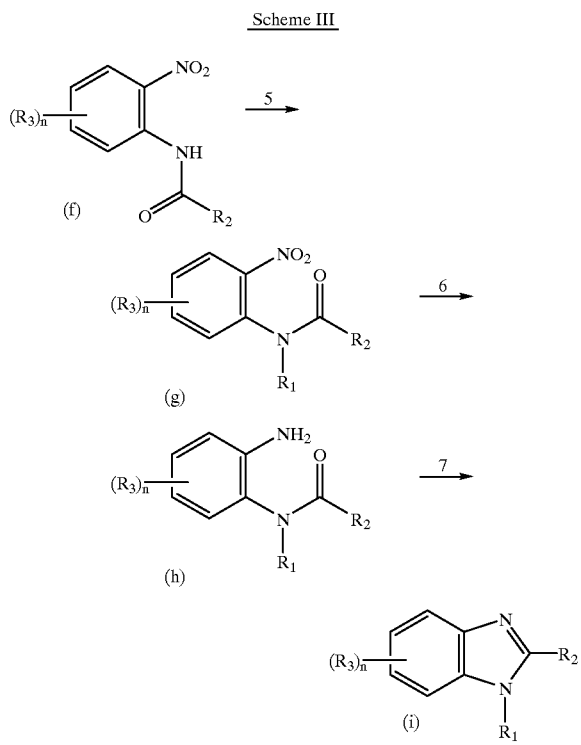

A substituted amide (f) is allowed to react with a base such as sodium hydride, lithium diisopropylamide. Reaction (reaction 5) with a compound expressed by $R_2Z$ (Z represents a halogen atom or a sulfonyl chloride.) gives the tertiary amide (g). There are several methods to obtain a compound of the formula (h) (reaction 6). (A) Reduction with iron or zinc under an acidic condition, (B) reduction with a transition metal catalyst primarily exemplified by palladium, platinum, ruthenium, and nickel under a hydrogen environment, (C) reduction with a transition metal catalyst primarily exemplified by palladium, platinum, ruthenium, and nickel under a presence of formic acid, or (D) reduction with sodium hydrosulfite. In many cases when method (A) is used, a compound of the formula (h) is reduced within the reaction system to directly produce a compound of the formula (i). Some compounds may partially produce a compound of the formula (i) under any condition in the methods (A) through (D). A compound of the formula (i) is produced from a compound of the formula (h) with a carboxylic acid such as acetic acid, p-toluenesulfonic acid, or an inorganic acid such as hydrochloric acid, sulfuric acid, or phosphoric acid, or sulfonic acid such as (reaction 7).

To obtain compounds in which $R_3$ is a substituted carbamoyl rest, the following scheme IV is employed:

Scheme IV

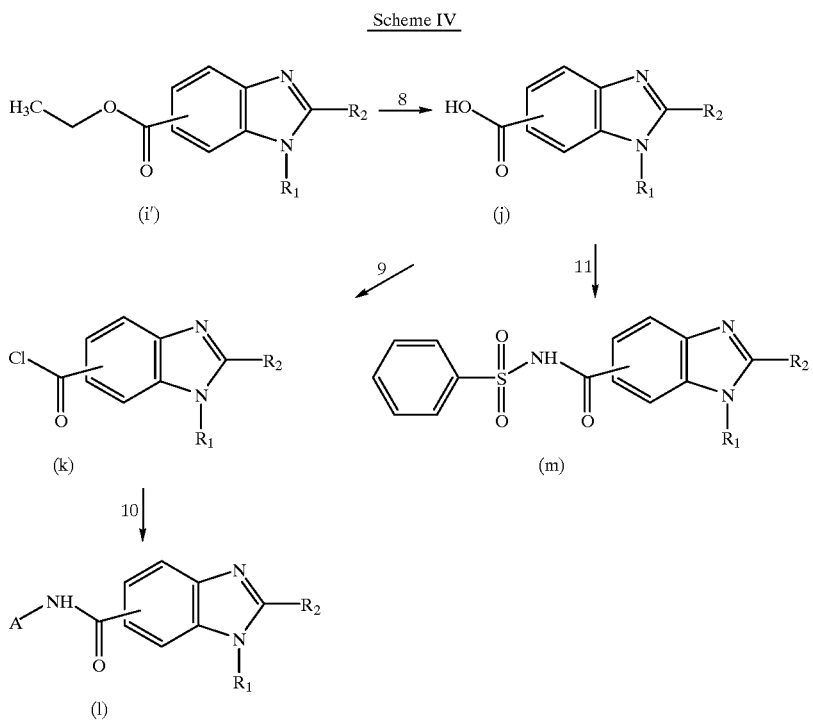

The ester (i') is saponified to the corresponding acid (j) by refluxing with sodium hydroxide and subsequent neutralisation with HCl (reaction 8). The acid chloride (k) is obtained (reaction 9) by allowing the acid (j) to react with oxalylchloride or thionylchloride. The amination (reaction 10) is performed by reaction of the acid chloride (k) with the amine $A-NH_2$ (and A is phenyl, benzyl, pyridyl or methylpyridyl) and triethylamine to give the amide (l). If A is benzenesulfonyl, the amination is performed on the acid (j) using N,N-carbonyldiimidazole in dimethylformamide, benzenesulfonamide and diazabicyclo-undecene (reaction 11).

The foregoing may be better understood from the following examples that are presented for the purposes of illustration and are not intended to limit the scope of the invention. As used in the following examples, the references to substituents such as $R_1$, $R_2$, etc. refer to the corresponding substituents in Formula I above.

EXAMPLE 1

2-(3,4,5-Trimethoxyphenyl)-1H-Benzimidazole

To a solution of 1,2-phenylenediamine (30 mmole, 3.24 g) and 3,4,5-trimethoxybenzaldehyde (30 mmole, 5.89 g) in acetonitrile (75 ml) is added 2,3-dichloro-5,6-dicyano-1,4-benzoquinone (DDQ) (30 mmole, 6.81 g), and the mixture is stirred 18 hours at room temperature. Sodium hydroxide (0.5M, 120 ml) is added, and the mixture is stirred over night at room temperature. The dark precipitate is filtered off and is digested with ethanol (30 ml) to give the title product as a brown solid (14%). ($R_1$=hydrogen, $R_2$=3,4,5-trimethoxyphenyl, n=0). $^1$H-NMR (DMSO, TMS, $\delta$): 3.74 (s, 3H, $OCH_3$), 3.91 (s, 6H, $OCH_3$), 7.20 (m, 2H, ar), 7.54 (s, 2H, ar), 7.61 (m, 2H, ar).

EXAMPLE 2

2-(3,4,5-Trimethoxyphenyl)-1H-5-Methoxybenzimidazole (A) N-(2-Nitro-4-methoxyphenyl)(3,4,5-trimethoxybenzamide)

To a solution of 4-methoxy-2-nitroaniline (45 mmole, 6.8 g) in dichloromethane (120 ml) and pyridine (75 mmole, 6 ml) is added 3,4,5-trimethoxybenzoylchloride (50 mmole, 11.5 g) in dichloromethane (40 ml). The mixture is stirred at room temperature over night. The precipitate is filtered off and dried in vacuo to yield the title product as an orange solid (74%).

(B) 2-(3,4,5-Trimethoxyphenyl)-1H-5-methoxybenzimidazole

To a suspension of N-(2-Nitro-4-methoxyphenyl)(3,4,5-trimethoxybenzamide) (13.8 mmole, 5.0 g) in acetic acid (60 ml) is added Fe (44 mmole, 2.5 g) in one portion, and the mixture is stirred under reflux one hour. The solvent is evaporated, ethyl acetate (75 ml) and saturated sodium bicarbonate (5×25 ml) is added. Excess Fe is removed by a stirring bar. The aqueous layer is extracted with ethyl acetate (2×50 ml) and the combined organic layers are washed with water (100 ml), dried with $MgSO_4$, filtered off and evaporated. Digestion in ethyl acetate, reflux (10 min.), filtration and evaporation in vacuo yields the title product (63%) ($R_1$=hydrogen, $R_{2=3,4,5}$-trimethoxyphenyl, $R_3$=$OCH_3$, n=1). $^1$H-NMR ($CDCl_3$, TMS, $\delta$): 3.52 (s, 6H, $OCH_3$), 3.79 (s, 3H, $OCH_3$), 3.82 (s, 3H, $OCH_3$), 6.90 (dd, 1H, ar, $J_{A,B}$=2.1 Hz, $J_{A,C}$=9 Hz), 7.08 (br, 1H, ar), 7.40 (s, 2H, ar), 7.48 (br, 1H, ar).

EXAMPLE 3

Ethyl 2-[5-Methoxy-2-(3,4,5-Trimethoxyphenyl) Benzimidazolyl]Acetate

Sodium hydride (11.45 mmole, 0.46 g, 60% in mineral oil) is dissolved in DMA (12 ml). A solution of 2-[3,4,5-trimethoxyphenyl]-1H-5-methoxybenzimidazole (7.63 mmole, 2.40 g) in DMA (12 ml) is slowly added under ice cooling. The suspension is stirred one hour. Ethyl-2-bromoacetate (11.45 mmole, 1.27 ml) in DMA (5 ml) is added under cooling. The mixture is stirred at room temperature over night. The solution is added dropwise onto ice (200 g) to form a fine precipitate, which is filtered off and dried in vacuo (67%). ($R_1$=$CH_2$—C(O)—OEt, $R_2$=3,4,5-trimethoxyphenyl, $R_3$=$OCH_3$, n=1). $^1$H-NMR ($CDCl_3$, TMS, $\delta$): 1.28 (t, 3H, $CH_3$, J=7.2 Hz), 3.92 (m, 12H, $OCH_3$), 4.30 (q, 2H, $CH_2$, J=7.2 Hz), 4.87 (s, 2H, $CH_2$), 6.95 (s, 2H, ar), 6.77–7.71 (m, 3H, ar).

EXAMPLE 4

2-[5-Methoxy-2-(3,4,5-Trimethoxyphenyl) Benzimidazolyl]N-benzylethanamide

Sodium hydride (4.77 mmole, 191 mg, 60% in mineral oil) is dissolved in DMA (7 ml). A solution of 2-[3,4,5-trimethoxyphenyl]-1H-5-methoxybenzimidazole (3.18 mmole, 1.0 g) in DMA (7 ml) is slowly added under ice cooling. The suspension is stirred one hour. 2-Bromo-N-acetamide (4.77 mmole, 1.09 g) in DMA (3 ml) is added under cooling. The mixture is stirred at room temperature over night. The solution is added dropwise onto ice (200 g) to form a fine precipitate, which is filtered off and dried in vacuo. Recrystallisation in ethyl acetate yields the pure title product (50%) ($R_1$=$(CH_2)_x$—C(O)—NH—$(CH_2)_x$—$R_5$, x=1, y=1, $R_5$=phenyl, $R_2$=3,4,5-trimethoxyphenyl, $R_3$=$OCH_3$, n=1). $^1$H-NMR (DMSO, TMS, $\delta$): 3.54 (m, 12H, $OCH_3$), 4.13 (m, 2H, $CH_2$), 4.76 (s, 2H, $CH_2$), 6.86 (s, 2H, ar), 6.67–7.37 (m, 8H, ar), 8.72 (m, 1H, NH).

EXAMPLE 5

Ethyl 2-[5-Fluoro-2-(3,4,5-Trimethoxyphenyl) Benzimidazolyl]Acetate (A) N-(2-Nitro-4-fluorophenyl)(3,4,5-trimethoxybenzamide)

To a solution of pyridine (96.1 mmole, 7.8 ml) in dichloromethane (160 ml) 4-fluoro-2-nitroaniline (64.05 mmole, 10 g) is added. Then 3,4,5-trimethoxybenzoyl chloride (76.86 mmole, 17.73 g) is added slowly to the mixture, and the mixture is stirred for two days at room temperature. The mixture is washed three times with 10% HCl. The organic layer is dried with $Na_2SO_4$, filtered and evaporated. Recrystallisation from dichloromethane gives the title compound as light yellow crystals (97%).

(B) 2-(3,4,5-Trimethoxyphenyl)-1H-5-Methoxybenzimidazole

To a solution of N-(2-nitro-4-fluorophenyl)(3,4,5-trimethoxybenzamide) (14.27 mmole, 5.0 g) in acetic acid (100 ml), iron (71.35 mmole 3.98 g) is added, and the mixture is refluxed for one hour and is stirred at room temperature over night. The solvent is evaporated and ethyl acetate (100 ml) is added. Saturated $NaHCO_3$ is added, and the organic layer is washed with water, is dried over $Na_2SO_4$, is filtered and evaporated. Recrystallisation from ethyl acetate yields the title product as yellow crystals (92%).

(C) Ethyl 2-[5-fluoro-2-(3,4,5,-trimethoxyphenyl) benzimidazolyl]acetate

To a solution of 2-(3,4,5-trimethoxyphenyl)-1H-5-methoxybenzimidazole (5.41 mmole, 1.7 g) in DMA (9 ml) at 0° C. sodium hydride (8.11 mmole, 0.2 g) in DMA (9 ml) is added dropwise under $N_2$. The mixture is stirred one hour. Ethyl 2-bromo-acetate (8.14 mmole, 1.36 g) in DMA (5 ml) is added in an ice bath. The reaction mixture is stirred over night at room temperature, and is added dropwise onto ice (400 g). The precipitate is filtered off, is dissolved with dichloromethane and is washed with water. The organic layer is dried with $Na_2SO_4$, is filtered and is evaporated. Recrystallisation from ethyl acetate gives the title compound ($R_1=(CH_2)_x—C(O)—OR_4$, x=1, $R_2$=3,4,5-trimethoxyphenyl, $R_3$=F, $R_4$=ethyl, n=1).

EXAMPLE 6

2-[5-Fluoro-2-(3,4,5-Trimethoxyphenyl) Benzimidazolyl]Acetic Acid

A mixture of ethyl 2-[5-Fluoro-2-(3,4,5-trimethoxyphenyl)benzimidazolyl]acetate (11.99 mmole, 4.65 g) and potassium hydroxide (40 mmole, 2.24 g) in ethanol (80 ml) is stirred at reflux for 2 hours. The solvent is evaporated and the residue is charged with water (100 ml) and ether (100 ml). The aqueous layer is washed with ether (2×50 ml) and charged with concentrated HCl (pH 1). After 24 hours the colorless precipitate is filtered off and dried in vacuo ($R_1=(CH_2)_x—C(O)—OR_4$, x=1, $R_2$=3,4,5-trimethoxyphenyl, $R_3$=F, $R_4$=hydrogen, n=1).

EXAMPLE 7

2-[5-Fluoro-2-(3,4,5-Trimethoxyphenyl) Benzimidazolyl]N-Benzylethanamide

A mixture of 2-[5-fluoro-2-(3,4,5-trimethoxyphenyl) benzimidazolyl]acetic acid (1.8 mmole, 650 mg) in DMA (5 ml), 1-(3-dimethylaminopropyl)-3-ethylcarbodiimide HCl (2.7 mmole, 0.52 g) and benzylamine (2.52 mmole, 0.28 ml) is stirred at room temperature for 22 hours. The reaction mixture is added dropwise onto ice (50 g), and the precipitate is filtered off and dried in vacuo ($R_1=(CH_2)_x—C(O)—NH—(CH_2)_y—R_5$, x=1, $R_5$=phenyl, $R_2$=3,4,5-trimethoxyphenyl, $R_3$=F, n=1, y=1).

EXAMPLE 8

2-Benzyl-1-(2-Methylpropyl)-5-Methoxybenzimidazole (A) 4-Methoxy-2-nitrophenyl-N-phenylacetamide 4-Methoxy-2-nitroaniline (47.6 mmole, 8.0 g) is added to a solution of pyridine (71.4 mmole, 5.8 ml) in dichloromethane (130 ml). Phenylacetyl chloride (40.6 mmole, 6.3 ml) in dichloromethane (40 ml) is slowly added, and the mixture is stirred at room temperature for two days. The mixture is washed with 10% HCl (3×), the organic layer is dried with $Na_2SO_4$, is filtered and evaporated. Recrystallisation from ethyl acetate gives the title product.

(B) 2-Benzyl-5-methoxybenzimidazole

Iron (Fe) (124.7 mmole, 6.97 g) is added to a solution of N-(4-methoxy-2-nitrophenyl) phenylacetamide (18.5 mmole, 5.0 g) in acetic acid (130 ml). The mixture is refluxed for two hours and is stirred at room temperature for 48 hours. The solvent is evaporated. Recrystallisation from ethyl. acetate gives the title product as a light yellow solid.

(C) 2-Benzyl-1-(2-methylpropyl)-5-methoxybenzimidazole

Sodium hydride (18.31 mmole, 0.44 g, 60% in mineral oil) is added in small amounts under nitrogen to an ice cooled solution of 2-benzyl-5-methoxybenzimidazole (16.64 mmole, 3.96 g) in dry DMA (9 ml). The mixture is stirred at the same temperature for 30 minutes. 1-Bromo-2-methylpropane (18.31 mmole, 2.51 g) in DMA (4 ml) is added in several portions, and the mixture is allowed to stir at room temperature over night. The reaction mixture is added dropwise onto ice. The precipitate is collected and dissolved in dichloromethane. The organic solution is washed several times with water, is dried with $Na_2SO_4$, is filtered and is evaporated to give the title compound ($R_1$= 2-methylpropyl, $R_2$=benzyl, $R_3$=$OCH_3$, n=1).

EXAMPLE 9

1-(2-Chlorobenzyl)-6-ethoxycarbonyl-2-phenylbenzimidazole (A) 3-Benzoylamino-4-nitro-ethylbenzoate Benzoyl chloride (4.6 ml) is added to a mixture of 3-amino-4-nitro-ethylbenzoate (18.4 g) and N,N-dimethylaniline (200 ml) under ice-chilled conditions, and the solution is stirred for 2 hours at room temperature. It is stirred for another 2 hours at 50° C. The reaction solution is poured into the cold 1N-hydrochloric acid, and then extraction is performed with ethyl acetate twice. After the organic layer is washed with 1N-hydrochloric acid, then with water, and dried, the solvent is removed through evaporation under reduced pressure. The residue is purified using silica gel column chromatography (eluate: ethyl acetate/hexane=1/ 10~1/4) and thus, 3-benzoylamino-4-nitro-ethylbenzoate (19.6 g) is obtained. $^1$H-NMR (CDCl$_3$, δ): 1.42 (3H, t, J=7.1 Hz), 2.32 (3H, s), 4.43 (2H, q, J=7.1 Hz), 7.82 (1H, dd, J=1.8 and 8.7 Hz), 8.25 (1H, d, J=8.7 Hz), 9.35 (1H, d, J=1.8 Hz), 10.19 (1H, s).

(B) 3-[N-(2-Chlorobenzyl)benzoylamino]-4-nitro-ethylbenzoate

In a nitrogen environment and at room temperature, sodium hydride (100 mg, 60% oil suspension) is added to an N,N-dimethylformamide (10 ml) solution of 3-benzoylamino-4-nitro-ethylbenzoate (450 mg) in a number of separate repetitions. The reaction suspension is stirred for 1 hour at the same temperature. The N,N-dimethylformamide (2 ml) solution of 2-chlorobenzylbromide (243 mg) is gradually dripped over a 10 minute span. After the reaction mixture is stirred for 1 hour at room temperature, it is then poured into ice water. Precipitated oily material is extracted with methylene chloride. The organic solvent layer is washed with water, dried, and then concentrated under reduced pressure. The residue is developed through silica gel flash column chromatography, and extraction is performed using 25% ethyl acetate/n-hexane.

Thus, yellow crystals of 3-[N-(2-chlorobenzyl) benzoylamino]-4-nitro-ethylbenzoate (480 mg) are obtained. $^1$H-NMR (CDCl$_3$, δ): 1.35 (3H, t, J=8 Hz), 4.35 (2H, q, J=8 Hz), 4.76 (1H, bd, J=15 Hz) 5.82 (1H, bd, J=15 Hz), 7.10–8.00 (12H, m). mp: 111–113° C.

(C) 1-(2-Chlorobenzyl)-6-ethoxycarbonyl-2-phenylbenzimidazole (44)

3-[N-(2-chlorobenzyl) benzoylamino]-4-nitro ethylbenzoate (460 mg) and reduced iron (210 mg) are added to the mixture solution of acetic acid (1 ml) and ethanol (2 ml), then the suspension is refluxed for one hour while being stirred briskly. After the reaction, the reaction solution is cooled, separated through filtration using celite, and then the filtrate is concentrated through evaporation under reduced pressure. Ethyl acetate and sodium bicarbonate are added to the residue, and the mixture separated into layers. After the organic layer is dried, the solvent is removed through evaporation under reduced pressure, and a brown residue is obtained. The residue is purified through flash column chromatography, and yellow crystals of 1-(2-chlorobenzyl)-6-ethoxycarbonyl-2-phenylbenzimidazole (44) (220 mg) are obtained.

$^1$H-NMR (CDCl$_3$, δ): 1.40 (3H, t, J 8 Hz), 4.38 (2H, q, J=8 Hz), 5.56 (2H, s), 6.72 (H, dd, J=1,8 Hz), 7.18(1H, dt, J=1,8 Hz), 7.30(1H, dt, J=1,8 Hz), 7.45–7.55 (4H, m), 7.64 (1H, d, J=1 Hz), 7.68 (1H, d, J=1 Hz), 7.90 (1H, d, J=10 Hz), 7.95 (1H, s), 8.08 (1H, dd, J=1, 8 Hz).

mp=140–142° C. (R$_1$=2-Chlorobenzyl, R$_2$=phenyl, R$_3$=ethoxycarbonyl, n=1)

EXAMPLE 10

2-Benzyl-6-ethoxycarbonyl-1-methylbenzimidazole (A) 4-Nitro-3-phenylacetylamino-ethylbenzoate Phenylacetyl chloride (1.87 g) is added to a mixture of 3-amino-4-nitro-ethylbenzoate (2.02 g) and N,N-dimethylaniline (200 ml) under ice-chilled conditions, and the solution is stirred for 2 hours at room temperature. It is stirred for another 2 hours at 50° C. The reaction solution is poured into the cold 1N-hydrochloric acid, and then extraction is performed with ethyl acetate twice. After the organic layer is washed with 1N-hydrochloric acid, then with water, and dried, the solvent is removed through evaporation under reduced pressure. The residue is purified using silica gel column chromatography (eluate: ethyl acetate/hexane=1/10~1/4) and thus, 4-nitro-3-phenylacetylamino-ethylbenzoate (3.30 g) is obtained. $^1$H-NMR (CDCl$_3$, δ): 1.41 (3H, t, J=7.2 Hz), 3.85 (2H, s), 4.42 (2H, q, J=7.2 Hz), 7.34–7.49 (5H, m), 7.79 (1H, m), 8.19 (1H, d, J=8.7 Hz), 9.39 (1H, d, J=1.6 Hz), 10.15 (1H, s).

(B) 2-Benzyl-6-ethoxycarbonyl-1-methylbenzimidazole

60% sodium hydride (0.166 g) is added to an N,N-dimethylformamide (10 ml) solution of 4-nitro-3-phenylacetylamino-ethylbenzoate (0.924 g) in an ice bath, and the solution is stirred for 1 hour at room temperature. Methyl iodide (0.50 ml) is added to the solution and the solution is stirred for 1 hour at room temperature. The reaction solution is poured into cooled 1N-hydrochloric acid, and extraction is performed with ethyl acetate twice. The organic layer is washed with 1N-hydrochloric acid and then washed with water. After it is dried, its solvent is removed through evaporation under reduced pressure. The residue is purified using silica gel column chromatography (eluate: ethyl acetate/hexane=1/10~1/4), and thus, 4-nitro-3-[N-(methyl)phenylacetylamino]-ethylbenzoate (0.510 g) is obtained. Ethanol (2 ml), acetic acid (1 ml), and reduced iron (0.240 g) are added to this material (0.148 g), and it is refluxed for 2 hours. After the solids are separated through filtration and its filtrate is concentrated, it is purified using fractional thin film silica gel chromatography (development solvent: chloroform/ethyl acetate=2/1), and thus, 2-benzyl-6-ethoxycarbonyl-1-methylbenzimidazole (115) (0.090 g) is obtained. $^1$H-NMR (CDCl$_3$, δ): 1.41 (3H, t, J=7.1 Hz), 3.63 (3H, s), 4.32 (2H, s), 4.40 (2H, q, J=7.1 Hz), 7.21–7.26 (3H, m), 7.27–7.32 (2H, m), 7.72 (1H, d, J=8.4 Hz), 7.98 (1H, dd, J=1.5 and 8.4 Hz), 8.03 (1H, d, J =1.3 Hz).

(R$_1$=methyl, R$_2$=benzyl, R$_3$=ethoxycarbonyl, n=1)

EXAMPLE 11

2-Benzyl-5-ethoxycarbonylbenzimidazole (A) 3-Nitro-4-phenylacetylamino-ethylbenzoate Phenylacetyl chloride (3.74 g) is added to a mixture of 4-amino-3-nitro-ethylbenzoate (4.04 g) and N,N-dimethylaniline (200 ml) under ice-chilled conditions, and the solution is stirred for 2 hours at room temperature. It is stirred for another 2 hours at 50° C. The reaction solution is poured into the cold 1N-hydrochloric acid, and then extraction is performed with ethyl acetate twice. After the organic layer is washed with 1N-hydrochloric acid, then with water, and dried, the solvent is removed through evaporation under reduced pressure. The residue is purified using silica gel column chromatography (eluate: ethyl acetate/hexane=1/10~1/4) and thus, 3-nitro-4-phenylacetylamino-ethylbenzoate (6.00 g) is obtained.

(B) 2-Benzyl-5-ethoxycarbonylbenzimidazole

A mixture of 3-nitro-4-phenylacetylamino-ethylbenzoate (3.60 g), ethanol (47 ml), acetic acid (23 ml) and reduced iron (6.4 g) is refluxed for four hours. Solids are separated through filtration and the filtrate is concentrated. Ethanol (50 ml) and 35% hydrochloric acid (5 g) are added to the residue and the solution is refluxed for 40 hours. The solution is neutralized with sodium bicarbonate and chloroform extraction is performed. The organic layer is concentrated under reduced pressure and then purified using silica gel column chromatography. Thus, 2-benzyl-5-ethoxycarbonylbenzimidazole (2.30 g) is obtained. $^1$H-NMR (CDCl$_3$, δ): 1.39 (3H, t, J=7.1 Hz), 4.26 (2H, s), 4.37 (2H, q, J=7.1 Hz), 7.22–7.36 (5H, m), 7.50 (1H, d, J=8.6 Hz), 7.94 (1H, dd, J=1.5 and 8.6 Hz), 8.23 (1H, d, J=1.3 Hz).

(R$_1$=hydrogen, R$_2$=benzyl, R$_3$=ethoxycarbonyl, n=1)

EXAMPLES 12 AND 13

2-Benzyl-1-(2,4-Dichlorobenzyl)-6-Ethoxycarbonylbenzimidazole and 2-Benzyl-1-(2,4-Dichlorobenzyl)-5-Ethoxycarbonylbenzimidazole N,N-dimethylformamide (15 ml), 2,4-dichlorobenzyl bromide (4.45 g) and sodium bicarbonate (1.23 g) are added to 2-benzyl-5-ethoxycarbonyl-benzimidazole (2.37 g) (example 11) and the solution is heated for one hour at 60° C. After adding ethyl acetate (70 ml) and water (70 ml) and separating the solution, the organic layer is washed with water three times and extraction is performed on the aqueous layer using ethyl acetate three times. By concentrating the obtained organic layer under reduced pressure, a mixture of 2-benzyl-1-(2,4-dichlorobenzyl)-6-ethoxycarbonylbenzimidazole (0.49 g) and 2-benzyl-1-(2,4-dichlorobenzyl)-5-ethoxycarbonylbenzimidazole (0.52 g) is obtained. Separation and purification is performed using medium pressure silica gel column chromatography (eluate: hexane/ethyl acetate=1/4~0/100).

EXAMPLE 12

$^1$H-NMR (CDCl$_3$, δ): 1.39 (3H, t), 4.24 (2H, s), 4.37 (2H, q), 5.32 (2H, q, 6.08 (1H, d, J=8.3 Hz), 6.90 (1H, d, J=8.4 Hz), 7.12–7.24 (5H, m), 7.41 (1H, s), 7.84 (1H, d, J=8.4 Hz), 7.88 (1H, s), 8.03 (1H, d, J=8.4 Hz).

(R$_1$=2,4-dichlorobenzyl, R$_2$=benzyl, R$_3$=ethoxycarbonyl, n=1).

EXAMPLE 13

$^1$H-NMR (CDCl$_3$, δ): 1.42 (3H, t, J=7.1 Hz), 4.25 (2H, s), 4.41 (2H, q, J=7.1 Hz), 5.28 (2H, s), 6.07 (1H, d, J=8.4 Hz), 6.90 (1H, dd, J=1.9 and 8.4 Hz), 7.08–7.28 (6H, m), 7.40 (1H, d, J=2.1 Hz), 7.96 (1H, dd, J=1.3 and 8.3 Hz), 8.56 (1H, d, J=0.9 Hz).

($R_1$=2,4-dichlorobenzyl, $R_2$=benzyl, $R_3$=ethoxycarbonyl, n=1).

EXAMPLE 14

2-Benzyl-5-Carboxy-1-(2,4-Dichlorobenzyl) Benzimidazole

Ethanol (80 ml) and 10% sodium hydroxide aqueous solution (37 g) are added to 2-benzyl-1-(2,4-dichlorobenzyl)-5-ethoxycarbonylbenzimidazole (0.50 g) (example 13) and the solution is refluxed for 4 hours. After the reaction solution is cooled, its acidity is adjusted to pH 6 with 10% hydrochloric acid. The sediment is gathered, washed with water, dried under reduced pressure, and thus, 2-benzyl-5-carboxy-1-(2,4-dichlorobenzyl) benzimidazole (0.40 g) is obtained.

$^1$H-NMR (DMSO-d6, δ): 4.28 (2H, s), 5.55 (2H. s), 6.19 (1H, d, J=8.4 Hz), 7.08–7.22 (6H, m), 7.41(11H, d, J=8.4 Hz), 7.62 (1H, d, J=2.2 Hz), 7.79 (1H, dd, J=1.5 and 8.6 Hz), 8.22 (1H, s), 12.72 (1H, br s).

($R_1$=2,4-dichlorobenzyl, $R_2$=benzyl, $R_3$=carboxyl, n=1).

EXAMPLE 15

2-Benzyl-6-Carboxy-1-(2,4-Dichlorobenzyl) Benzimidazole

Ethanol (80 ml) and 10% sodium hydroxide aqueous solution (37 g) are added to 2-benzyl-1-(2,4-dichlorobenzyl)-6-ethoxycarbonylbenzimidazole (0.48 g) (example 12), and the solution is refluxed for 4 hours. After the reaction solution is cooled, its acidity is adjusted to pH 6 with 10% hydrochloric acid. The sediment is gathered, is washed with water, is dried under reduced pressure, and thus, 2-benzyl-6-carboxy-1-(2,4-dichlorobenzyl) benzimidazole (0.35 g) is obtained.

$^1$H-NMR (DMSO-d6, δ): 4.30 (2H, s), 5.61 (2H. s), 6.19 (1H, d, J=8.4 Hz), 7.09–7.22 (6H, m), 7.64 (1H, d, J=2.1 Hz), 7.71 (1H, d, J=8.4Hz), 7.82 (1H, dd, J=1.5 and 8.4 Hz), 7.94 (1H, d, J=1.2 Hz), 12.78 (1H, br s).

($R_1$=2,4-dichlorobenzyl, $R_2$=benzyl, $R_3$=carboxyl, n=1).

EXAMPLES 16 AND 17

2-Benzyl-1-(2-Chlorobenzyl)-6-Ethoxycarbonylbenzimidazole and 2-Benzyl-1-(2-Chlorobenzyl)-5-Ethoxycarbonylbenzimidazole N,N-dimethylformamide (15 ml), 2-chlorobenzyl bromide (3.94 g) and sodium bicarbonate (1.23 g) are added to 2-benzyl-5-ethoxycarbonyl-benzimidazole (2.37 g) (example 11) and the solution is heated for one hour at 60° C. After adding ethyl acetate (70 ml) and water (70 ml) and separating the solution, the organic layer is washed with water three times and extraction is performed on the aqueous layer using ethyl acetate three times. By concentrating the obtained organic layer under reduced pressure, a mixture of 2-benzyl-1-(2-chlorobenzyl)-6-ethoxycarbonylbenzimidazole (1.06 g) and 2-benzyl-1-(2-chlorobenzyl)-5-ethoxycarbonylbenzimidazole (0.640 g) is obtained. Separation and purification is performed using medium pressure silica gel column chromatography (eluate: hexane/ethyl acetate=1/4~0/100) produces medium pressure silica gel column chromatography (eluate: hexane/ethyl acetate=1/4~0/100).

EXAMPLE 16

$^1$H-NMR (CDCl$_3$, δ): 1.83 (3H, t, J=7.1 Hz), 4.23 (2H, s), 4.3 (2H, q, J=7.1 Hz), 5.36 (2H, s), 6.23 (1H, d, J=7.8 Hz), 6.97 (1H, d, J=7.6 Hz), 7.11–7.45 (7H, m), 7.85 (1H, d, J=8.5 Hz), 7.91 (1H, s), 8.02 (1H, dd, J=1.2 and 8.6 Hz).

($R_1$=2-chlorobenzyl, $R_2$=benzyl, $R_3$=ethoxycarbonyl, n=1)

EXAMPLE 17

$^1$H-NMR (CDCl$_3$, δ): 1.41 (3H, t, J=7.1 Hz), 4.25 (2H, s), 4.41 (2H, q, J=7.1 Hz), 5.33 (2H, s), 6.22 (1H, d, J=6.9 Hz), 6.97 (1H, t, J=7.6 Hz), 7.12–7.28 (7H, m), 7.40 (1H, d, J=8.0 Hz), 7.95 (1H, dd, J=1.6 and 8.6 Hz), 8.60 (1H, d, J=1.4 Hz).

($R_1$=2-chlorobenzyl, $R_2$=benzyl, $R_3$=ethoxycarbonyl, n=1).

EXAMPLE 18

2-Benzyl-1-Methyl-6-[(2-Pyridylmethyl)carbamoyl] Benzimidazole

A.) 2-Benzyl-6-carboxy-1-methylbenzimidazole Hydrochloride

To an ethanol (4 ml) solution of 2-benzyl-6-ethoxycarbonyl-1-methylbenzimidazole (0.340 g) (example 10), 5% sodium hydroxide aqueous solution (2.8 g) is added, and the solution is refluxed for 1.5 hours. The solution is made acidic using 1N hydrochloric acid, and is concentrated under reduced pressure. Ethanol is added to the residue and organic materials are extracted. The ethanol is removed under reduced pressure and thus, 2-benzyl-6-carboxy-1-methylbenzimidazole hydrochloride (0.30 g) is obtained.

$^1$H-NMR (DMSO-d6, δ): 4.00 (3H, s), 4.62 (2H, s), 7.33 (1H, m), 7.35–7.45 (4H, m), 7.83 (1H, d, J=8.4 Hz), 8.06 (1H, d, J=8.4 Hz), 8.42 (1H, s), 13.3 (1H, br s).

B.) 2-Benzyl-1-methyl-6-[(2-pyridylmethyl)carbamoyl] benzimidazole

Dichloromethane (15 ml) and a few drops of N,N-dimethylformamide are added to 2-benzyl-6-carboxy-1-methylbenzimidazole (0.310 g), and the solution is chilled with ice. Oxalyl chloride (0.295 g) is dripped into the solution, which is then stirred for a few minutes. After the solution is further stirred for 1.5 hours at room temperature, the solution is concentrated under reduced pressure to a third of its original volume.

Precipitants are collected and added to a dichloromethane (200 ml) solution of 2-aminomethylpyridine (0.108 g) and triethylamine (0.303 g) over a few doses while it is chilled with ice. After the solution is stirred for 15 hours, the reaction solution is washed with water (3×), and is further washed with a saturated sodium bicarbonate solution. The organic layer is concentrated under reduced pressure, and crystals are formed using ethyl acetate. The crystals are separated through filtration and dried, and 2-benzyl-1-methyl-6-[(2-pyridylmethyl)carbamoyl]benzimidazole (0.171 g) is obtained.

$^1$H-NMR (CDCl$_3$, δ): 3.66 (3H, t), 4.35 (2H, s), 4.80 (2H, d, J=4.8 Hz), 7.21–7.37 (7H, m), 7.66 (1H, br t), 7.67–7.73 (2H, m), 7.78 (1H, d, J=8.4 Hz), 7.98 (1H, s), 8.5 8 (1H, d, J=4.9 Hz).

IR(KBr): 1632 cm$^{-1}$.

mp: 168.5–169.5° C.

$R_1$=methyl, $R_2$=benzyl, $R_3$=(2-pyridylmethyl)carbamoyl, n=1).

EXAMPLE 19

5-Benzenesulfonylcarbamoyl-2-Benzyl-1-(2-Chlorobenzyl) Benzimidazole (A) 2-Benzyl-5-carboxy-1-(2-chlorobenzyl) benzimidazole Ethanol (8 ml) and 10% sodium hydroxide aqueous solution (3.7 g) are added to 2-benzyl-1-(2-chlorobenzyl)-5-ethoxycarbonylbenzimidazole (0.635 g) (example 16), and the solution is refluxed for 4 hours. After the reaction solution is cooled, its acidity is adjusted to pH 6 with 10% hydrochloric acid. The sediment is gathered, washed with water, dried under reduced pressure, and thus, 2-benzyl-5-carboxy-1-(2-chlorobenzyl) benzimidazole (143) (0.488 g) is obtained.

$^1$H-NMR (DMSO-d6, δ): 4.27 (2H, s), 5.57 (2H. s), 6.27 (1H, d, J=7.1 Hz), 7.06 (1H, t), 7.10–7.29 (6H, m), 7.39 (1H, d, J=8.6 Hz), 7.47 (1H, d, J=7.9 Hz), 7.78 (1H, dd, J=1.4 and 8.6 Hz), 8.21 (1H, d, J=1.2 Hz), 12.71 (1H, br s).

(B) 5-Benzenesulfonylcarbamoyl-2-benzyl-1-(2-chlorobenzyl) benzimidazole

N,N'-carbonyldiimidazole (0.401 g) is added all at once to an N,N-dimethylformamide (20 ml) solution of 2-benzyl-5-carboxy-1-(2-chlorobenzyl) benzimidazole (0.466 g), and the solution is stirred for one hour at room temperature. Subsequently, a N,N-dimethylformamide (5 ml) solution of benzenesulfonamide (0.389 g) and diazabicycloundecene (0.377 g) is added, and the solution is stirred for 48 hours at 100° C. The reaction solution is cooled, and the solvent is removed through evaporation under reduced pressure. This material is dissolved in a mixture solution of methanol and water. The pH is adjusted to pH 5~6 using 10% hydrochloric acid. Precipitated crystals are separated through filtration, and are dried. Thus, 5-benzenesulfonylcarbamoyl-2-benzyl-1-(2-chlorobenzyl)benzimidazole (0.447 g) is obtained.

$^1$H-NMR (DMSO-d6, δ): 4.28 (2H, s), 5.57 (2H, s), 6.23 (1H, d, J=7.6 Hz), 7.04 (1H, t, J=7.6 Hz), 7.10–7.26 (6H, m), 7.40 (1H, d, J=8.6 Hz), 7.46 (1H, d, J=8.0 Hz), 7.61–7.73 (4H, m), 8.00 (2H, d, J=7.6 Hz), 8.23 (1H, s), 12.43 (1H, br s).

IR(KBr): 1685 cm$^{-1}$.

mp: 152.0–155.0° C.

($R_1$=2-chlorobenzyl, $R_2$=benzyl, $R_3$=benzenesulfonyl carbamoyl, n=1).

EXAMPLE 20

6-Benzenesulfonylcarbamoyl-2-Benzyl-1-(2-Chlorobenzyl) Benzimidazole

By using the method of Example 18, 6-benzenesulfonylcarbamoyl-2-benzyl-1-(2-chlorobenzyl) benzimidazole (0.803 g) is obtained from 2-benzyl-6-carboxy-1-(2-chlorobenzyl)benzimidazole (0.760 g), N,N'-carbonyidiimidazole (0.654 g), benzenesulfonamide (0.634 g) and diazabicycloundecene (0.614 g).

$^1$H-NMR (DMSO-d6, δ): 4.41 (2H, s), 5.71 (2H, s), 6.32 (1H, d, J=7.7 Hz), 7.06 (1H, t, J=7.7 Hz), 7.14–7.30 (6H, m), 7.50 (1H, d, J=8.0 Hz), 7.62 (2H, t), 7.70 (1H, t), 7.81 (1H, d, J=8.6 Hz), 7.87 (1H, d, J=8.5 Hz), 7.97 (2H, d, J=8.2 Hz), 8.16 (1H, s), 12.60 (1H, br s).

IR(KBr): 1704 cm$^{-1}$.

mp: 143.0–144.5° C.

($R_1$=2-chlorobenzyl, $R_2$=benzyl, $R_3$=benzenesulfonyl carbamoyl, n=1).

EXAMPLE 21

6-Benzenesulfonylcarbamoyl-1-(Biphenyl-4-ylmethyl)-2-Phenylbenzimidazole (A) N-Benzenesulfonyl-3-amino-4-nitrobenzamide N,N'-carbonyldiimidazole (28.9 g) is added to an N,N-dimethylformamide (300 ml) solution of 3-acetylamino-4-nitro-benzoic acid (20.0 g), and the solution is stirred for 1 hour at room temperature. Further, benzenesulfonamide (28.0 g) and diazabicycloundecene (27.16 g) are added to the solution and the solution is stirred for 4 days at 100° C. The solvent is removed through evaporation under reduced pressure. Chloroform and 10% sodium hydroxide aqueous solution are added to the residue, and the mixture is stirred briskly. 10% hydrochloric acid is added to the aqueous layer until neutral. Chloroform is added and the solution is stirred briskly. The precipitated crystals are separated through filtration, and are dried. Thus, N-benzenesulfonyl-3-amino-4-nitrobenzamide (14.4 g) is obtained.

$^1$H-NMR (DMSO-d6, δ): 6.93 (1H, dd, J=1.8 and 9.0 Hz), 7.43 (1H, d, J=1.8 Hz), 7.52 (2H, br s), 7.65 (2H, t, J=7.5 Hz), 7.74 (1H, t, J=7.5 Hz), 7.98–7.82 (3H, m), 12.74 (1H, s).

(B) N-Benzenesulfonyl-3-(biphenyl-4-ylmethylamino)-4-nitrobenzamide potassium salt 20% potassium bicarbonate aqueous solution (56.5 g) and 4-bromomethyl biphenyl (11.5 g) are added to a methanol (150 ml) solution of N-benzenesulfonyl-3-amino-4-nitrobenzamide (10.0 g), and the solution is stirred for 3 hours at 70 ° C. The solution is cooled, its precipitated crystals are separated through filtration and dried, and N-benzenesulfonyl-3-(biphenyl-4-ylmethylamino)-4-nitrobenzamide potassium salt (4.27 g) is obtained.

$^1$H-NMR (DMSO-d6, δ): 4.65 (2H, d, J=5.8 Hz), 7.19 (1H, d, J=8.9 Hz), 7.33–7.42 (4H, m), 7.57–7.71 (4H, m), 7.75–7.81 (2H, m), 8.02 (1H, d, J=8.9 Hz), 8.61 (1H, br t).

IR(Nujol): 1598 cm$^{-1}$.

(C) N-Benzenesulfonyl-4-amino-3-(biphenyl-4-ylmethylamino) benzamide potassium salt 5% palladium/carbon (0.64 g) is added to a mixture of N-benzenesulfonyl-3-(biphenyl-4-ylmethylamino)-4-nitrobenzamide potassium salt (4.27 g), 20% potassium bicarbonate aqueous solution (10.7 g), and methanol (200 ml). The solution is then stirred for 14 hours at 35° C. under a hydrogen environment. The precipitated crystals are dissolved when a mixture solution of acetone and water (acetone/water=5/2, 400 ml) is added and its solids are separated through filtration. The filtrate is concentrated, the precipitated crystals are separated through filtration and are dried. Thus, N-benzenesulfonyl-4-amino-3-(biphenyl-4-ylmethylamino)benzamide potassium salt (3.15 g) is obtained.

$^1$H-NMR (DMSO-d6, δ): 4.31 (2H, d, J=5.7 Hz), 4.85 (2H, s), 4.91 (1H, br t, J=5.7 Hz), 6.45 (1H, d, J=7.9 Hz), 7.07 (1H, s), 7.13 (1H, d, J=7.9 Hz), 7.29–7.36 (4H, m), 7.43–7.47 (4H, m), 7.60 (2H, d, J=8.1 Hz), 7.65 (2H, d, J=7.6 Hz), 7.73–7.76 (2H, m).

IR (Nujol): 1574 cm$^{-1}$.

(D) 6-Benzenesulfonylcarbamoyl-1-(biphenyl-4-ylmethyl)-2-phenylbenzimidazole

Triethylamine (0.115 g) and benzoyl chloride (0.200 g) are added to an N,N-dimethylformamide (5 ml) solution of N-benzenesulfonyl-4-amino-3-(biphenyl-4-ylmethylamino) benzamide (0.50 g). After stirring the solution for 15 hours at room temperature, a potassium bicarbonate aqueous solution is added to halt the reaction. Under reduced pressure, the solvent is removed. The residue is dissolved in a mixture of water and methanol, and its acidity is adjusted to pH 5~6 with 10% hydrochloric acid. Precipitated crystals are collected, and dried. Preliminarily purified N-benzenesulfonyl-4-benzoylamino-3-(biphenyl-4-ylmethylamino)benzamide (0.393 g) is obtained, which is added to a mixture solvent of 10% hydrochloric acid (3.3 g), methanol (6 ml), and water (4 ml). Furthermore, 35% hydrochloric acid (0.5 g) is added and the solution is stirred for three hours at 60° C. After 20% potassium bicarbonate solution is added to turn the reaction solution into a basic, its acidity is adjusted to pH 5~6 with 10% hydrochloric acid. Precipitated crystals are separated through filtration, dried and thus, 6-benzenesulfonylcarbamoyl-1-(biphenyl-4-ylmethyl)-2-phenylbenzimidazole (0.270 g) is obtained.

$^1$H-NMR (DMSO-d6, δ): 5.70 (2H, s), 7.07 (2H, d, J=8.2 Hz), 7.32–7.37 (1H, m), 7.43 (2H, t, J=5.7 Hz), 7.53–7.58 (2H, m), 7.58–7.65 (7H, m), 7.68–7.72 (1H, m), 7.77 (2H, dd, J=7.5 and 1.5 Hz), 7.81–7.83 (2H, m), 7.98–8.02 (2H, m), 8.22 (1H, s), 12.47 (11H, s).

IR(KBr): 1690 cm$^{-1}$.

mp: 138.5–139.5 ° C.

($R_1$=biphenyl-4-ylmethyl, $R_2$=phenyl, $R_3$=benzenesulfonyl carbamoyl, n=1).

The compounds of this invention can be formulated with pharmaceutically acceptable carriers into unit dosage forms in a conventional manner so that the patient in need of therapy for precancerous lesions can periodically (e.g., once or more per day) take a compound according to the methods of this invention. The exact initial dose of the compounds of this invention can be determined with reasonable experimentation. It is believed that a dosage of from about 0.1 to 400 mg of such compounds for intravenous administration would achieve a therapeutic systemic circulatory concentration.

It will be understood that various changes and modifications can be made in the details of procedure, formulation and use without departing from the spirit of the invention, especially as defined in the following claims.

We claim:

1. A method of treating a mammal having precancerous lesions sensitive to a compound below comprising administering a pharmacologically effective amount of a compound of formula I or pharmaceutically acceptable salt thereof:

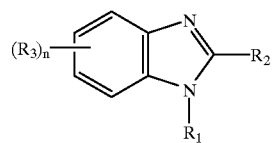

wherein $R_1$ is selected from a group consisting of hydrogen, lower alkyl, —$(CH_2)_x$—C(O)—$OR_4$, —$(CH_2)_x$—C(O)—NH—$(CH_2)_y$—$R_5$, $(CH_2)_x$—S(O)$_m$—$R_6$ or substituted or unsubstituted benzyl, wherein said substituents are one or two independently selected from a group consisting of halogen, lower alkyl, lower alkoxy or phenyl;

$R_2$ is substituted or unsubstituted aryl, wherein said aryl group is selected from the group consisting of phenyl, benzyl, pyridyl, pyrimidyl, pyrazinyl, imidazolyl, indolyl, triazinyl, tetrazolyl, thiophenyl, furanyl, pyrazolyl, or pyrrolyl, and wherein said substituents are one to three independently selected from the group consisting of halogen, lower alkyl or lower alkoxy;

$R_3$ is selected from a group consisting of halogen, lower alkoxy, lower alkyl, lower alkoxy carbonyl, carboxyl, substituted and unsubstituted carbamoyl, wherein said substituents are one or two independently selected from a group consisting of phenyl, benzyl, pyridyl, pyridylmethyl, or benzenesulfonyl;

$R_4$ is hydrogen or lower alkyl;

$R_5$ is selected from a group consisting of hydrogen, lower alkyl, benzyl, pyridyl, pyrimidinyl, pyrazinyl, imidazolyl, indolyl, triazinyl, tetrazolyl, thiophenyl, furanyl, thiazolyl, pyrazolyl, or pyrrolyl;

$R_6$ is substituted or unsubstituted phenyl, wherein said substituents are one to three independently selected from the group consisting of halogen, lower alkyl or lower alkoxy;

x is 0, 1, or 2;

m is 0, 1, or 2;

n is 0, 1 or 2; and y is 0, 1, or 2.

2. The method of claim 1 wherein:

$R_1$ is selected from a group consisting of hydrogen, lower alkyl, —$(CH_2)_x$—C(O)—$OR_4$, —$(CH_2)_x$—C(O)—NH—$(CH_2)_y$—$R_5$, or substituted or unsubstituted benzyl, wherein said substituents are one or two independently selected from the group consisting of halogen, lower alkoxy or phenyl;

$R_2$ is substituted or unsubstituted aryl, wherein said aryl group is selected from the group consisting of phenyl, benzyl, pyridyl, pyrimidyl, pyrazinyl, triazinyl, tetrazolyl, thiophenyl, furanyl, pyrazolyl, or pyrrolyl, and wherein said substituents are two or three independently selected from the group consisting of halogen and lower alkoxy;

$R_3$ is selected from a group consisting of halogen, lower alkoxy, lower alkoxy carbonyl, carboxyl, and substituted carbamoyl, wherein said substituent is one from a group consisting of phenyl, benzyl, pyridyl, pyridylmethyl, or benzenesulfonyl;

$R_4$ is lower alkyl;

$R_5$ is selected from a group consisting of benzyl, pyridyl, pyrimidinyl, pyrazinyl, triazinyl, tetrazolyl, thiophenyl, or furanyl;

$R_6$ is substituted phenyl, wherein said substituents are two or three independently selected from the group consisting of halogen or lower alkoxy;

x is 1 or 2;

m is 2;

n is 0 or 1; and y is 0 or 1.

3. The method of claim 1 wherein:

$R_1$ is selected from a group consisting of hydrogen, —$(CH_2)_x$—C(O)—$OR_4$, —$(CH_2)_x$—C(O)—NH—$(CH_2)_y$—$R_5$, or substituted benzyl, wherein said substituent is one selected from the group consisting of halogen or lower alkoxy;

$R_2$ is substituted aryl, wherein said aryl group is selected from the group consisting of phenyl, benzyl, pyridyl, pyrimidyl, pyrazinyl, and triazinyl, and wherein said substituents are three independently selected from the group consisting of lower alkoxy;

$R_3$ is selected from a group consisting of halogen, lower alkoxy, and substituted carbamoyl, wherein said substituent is one from a group consisting of benzyl, pyridylmethyl, or benzenesulfonyl;

$R_4$ is lower alkyl;

$R_5$ is selected from a group consisting of benzyl and pyridyl;

$R_6$ is substituted phenyl, wherein said substituents are three independently selected from the group consisting of lower alkoxy;

x is 1;

m is 2;

n is 1; and y is 0.

4. A method for inhibiting the growth of neoplastic cells sensitive to a compound below comprising exposing the cells to a growth inhibiting effective amount of a compound of Formula I

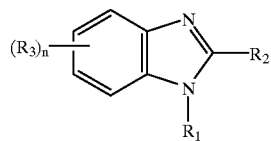

wherein $R_1$ is selected from a group consisting of hydrogen, lower alkyl, —(CH$_2$)$_x$—C(O)—OR$_4$, —(CH$_2$)$_x$—C(O)—NH—(CH$_2$)$_y$—R$_5$, (CH$_2$)$_x$—S(O)$_m$—R$_6$ or substituted or unsubstituted benzyl, wherein said substituents are one or two independently selected from a group consisting of halogen, lower alkyl, lower alkoxy or phenyl;

$R_2$ is substituted or unsubstituted aryl, wherein said aryl group is selected from the group consisting of phenyl, benzyl, pyridyl, pyrimidyl, pyrazinyl, imidazolyl, indolyl, triazinyl, tetrazolyl, thiophenyl, furanyl, pyrazolyl, or pyrrolyl, and wherein said substituents are one to three independently selected from the group consisting of halogen, lower alkyl or lower alkoxy;

$R_3$ is selected from a group consisting of halogen, lower alkoxy, lower alkyl, lower alkoxy carbonyl, carboxyl, substituted and unsubstituted carbamoyl, wherein said substituents are one or two independently selected from a group consisting of phenyl, benzyl, pyridyl, pyridylmethyl, or benzenesulfonyl;

$R_4$ is hydrogen or lower alkyl;

$R_5$ is selected from a group consisting of hydrogen, lower alkyl, benzyl, pyridyl, pyrimidinyl, pyrazinyl, imidazolyl, indolyl, triazinyl, tetrazolyl, thiophenyl, furanyl, thiazolyl, pyrazolyl, or pyrrolyl;

$R_6$ is substituted or unsubstituted phenyl, wherein said substituents are one to three independently selected from the group consisting of halogen, lower alkyl or lower alkoxy;

x is 0, 1, or 2;

m is 0, 1, or 2;

n is 0, 1 or 2; and y is 0, 1, or 2.

5. The method of claim 4 wherein:

$R_1$ is selected from a group consisting of hydrogen, lower alkyl, —(CH$_2$)$_x$—C(O)—OR$_4$, —(CH$_2$)$_x$—C(O)—NH—(CH$_2$)$_y$—R$_5$, or substituted or unsubstituted benzyl, wherein said substituents are one or two independently selected from the group consisting of halogen, lower alkoxy or phenyl;

$R_2$ is substituted or unsubstituted aryl, wherein said aryl group is selected from the group consisting of phenyl, benzyl, pyridyl, pyrimidyl, pyrazinyl, triazinyl, tetrazolyl, thiophenyl, furanyl, pyrazolyl, or pyrrolyl, and wherein said substituents are two or three independently selected from the group consisting of halogen and lower alkoxy;

$R_3$ is selected from a group consisting of halogen, lower alkoxy, lower alkoxy carbonyl, carboxyl, and substituted carbamoyl, wherein said substituent is one from a group consisting of phenyl, benzyl, pyridyl, pyridylmethyl, or benzenesulfonyl;

$R_4$ is lower alkyl;

$R_5$ is selected from a group consisting of benzyl, pyridyl, pyrimidinyl, pyrazinyl, triazinyl, tetrazolyl, thiophenyl, or furanyl;

$R_6$ is substituted phenyl, wherein said substituents are two or three independently selected from the group consisting of halogen or lower alkoxy;

x is 1 or 2;

m is 2;

n is 0 or 1; and y is 0 or 1.

6. The method of claim 4 wherein:

$R_1$ is selected from a group consisting of hydrogen, —(CH$_2$)$_x$—C(O)—OR$_4$, —(CH$_2$)$_x$—C(O)—NH—(CH$_2$)$_y$—R$_5$, or substituted benzyl, wherein said substituent is one selected from the group consisting of halogen or lower alkoxy;

$R_2$ is substituted aryl, wherein said aryl group is selected from the group consisting of phenyl, benzyl, pyridyl, pyrimidyl, pyrazinyl, and triazinyl, and wherein said substituents are three independently selected from the group consisting of lower alkoxy;

$R_3$ is selected from a group consisting of halogen, lower alkoxy, and substituted carbamoyl, wherein said substituent is one from a group consisting of benzyl, pyridylmethyl, or benzenesulfonyl;

$R_4$ is lower alkyl;

$R_5$ is selected from a group consisting of benzyl and pyridyl;

$R_6$ is substituted phenyl, wherein said substituents are three independently selected from the group consisting of lower alkoxy;

x is 1;

m is 2;

n is 1; and y is 0.

* * * * *